United States Patent [19]

Shen et al.

[11] 3,947,582

[45] Mar. 30, 1976

[54] PHENYLACETIC ACID COMPOUNDS IN TREATING ABNORMAL PLATELET AGGREGATION

[75] Inventors: Tsung-Ying Shen, Westfield, N.J.; Jorge P. Li, Brown Deer, Wis.; Conrad P. Dorn, Jr., Plainfield, N.J.

[73] Assignee: Merck & Co., Inc., Rahway, N.J.

[22] Filed: Feb. 10, 1975

[21] Appl. No.: 548,486

Related U.S. Application Data

[60] Division of Ser. No. 388,852, Aug. 16, 1973, Pat. No. 3,899,506, which is a continuation-in-part of Ser. No. 165,389, July 22, 1971, abandoned, which is a continuation-in-part of Ser. No. 71,227, Sept. 10, 1970, abandoned.

[52] U.S. Cl. .............................................. 424/272

[51] Int. Cl.$^2$........................................... A61K 31/42
[58] Field of Search .................................. 260/307 D

[56] References Cited
UNITED STATES PATENTS 3,816,443   6/1974   Dorn..................................... 260/304

*Primary Examiner*—Stanley J. Friedman
*Attorney, Agent, or Firm*—Stanley E. Anderson, Jr.; Mario A. Monaco; Harry E. Westlake, Jr.

[57] ABSTRACT

Pharmaceutical Compositions based on 4-(Benzoxazol-2-yl)phenylacetic acids, alcohols, esters, amides and their non-toxic pharmaceutically acceptable salts and method of treating abnormal platelet aggregation.

24 Claims, No Drawings

PHENYLACETIC ACID COMPOUNDS IN TREATING ABNORMAL PLATELET AGGREGATION

This application is a division of application Ser. No. 388,852 filed Aug. 16, 1973, now U.S. Pat. No. 3,899,506 which in turn is a continuation-in-part of U.S. Ser. No. 165,389, filed July 22, 1971, which in turn is a continuation-in-part of U.S. Ser. No. 71,227, filed Sept. 10, 1970, both are now abandoned.

This invention relates to a novel class of compounds. In addition it relates to a class of compounds useful in the treatment of inflammation, which also exhibit potent analgesic and antipyretic activity. Connected with their antiinflammatory activity, the novel compounds are also platelet aggregation inhibitors useful in the treatment and prevention of arterial thrombosis.

This invention also includes methods of treating inflammation in its varying manifestations, utilizing novel antiinflammatory compositions containing benzoxazole phenylacetic acids. In addition, these novel compositions exhibit potent analgesic and antipyretic activity and, therefore, this invention also relates to analgesic and antipyretic methods and compositions. Furthermore, this invention is concerned with use of the novel compositions for prevention of arterial thrombosis through inhibition of platelet aggregation.

The novel benzoxazole phenylactic acids are represented by the following formula:

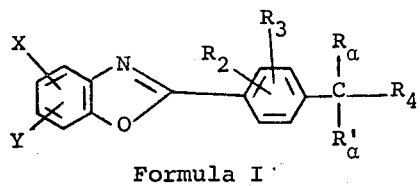

Formula I wherein
R $\alpha$ is hydrogen or methyl;
R $\alpha$ ' is hydrogen, or R $\alpha$ and R $\alpha$ ' taken together can be methylene; or R $\alpha$ ' can be a methylene linkage attached to the unsubstituted ortho position of the benzenoid ring;
X and Y are the same or different and each is hydrogen;
chloro; bromo; fluoro;
$C_{1-5}$ alkyl;
$C_{1-3}$ alkylsulfonyl;
nitro,
di($C_{1-3}$ alkyl)amino,
hydroxy, or
$C_{1-3}$ alkoxy;
$R_2$ and $R_3$ are the same or different and each is
hydrogen,
chloro,
bromo,
fluoro,
$C_{1-3}$ alkylthio,
nitro,
amino,
di($C_{1-3}$ alkyl)amino;
$R_4$ is COOH,
—$CH_2$—OH,
COOR, where R may be
$C_{1-5}$ alkyl,
$C_{2-5}$ alkenyl, such as vinyl, allyl, methallyl, etc.,
$C_{2-3}$ alkynyl, such as ethynyl, propynyl, etc.,
$C_{3-6}$ cycloalkyl, phenyl,
$C_{1-3}$ lower alkylphenyl,
carboxyphenyl,
carboxamidophenyl,
$C_{1-3}$ alkoxy $C_{1-3}$ alkyl,
hydroxy $C_{1-3}$ alkyl,
di($C_{1-3}$ alkyl)amino $C_{1-3}$ alkyl,
$\alpha$-tetrahydropyranyl,
$CONH_2$;

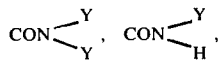

where Y may be $C_{1-3}$ alkyl,
hydroxy $C_{1-3}$ alkyl,
phenyl $C_{1-3}$ alkyl,
phenyl,
hydroxyphenyl,
cyclohexyl,
carboxymethyl,
and the pharmaceutically acceptable non-toxic addition salts thereof, with the proviso that if $R_4$ is —COOH, and R $\alpha$ is hydrogen, then one of X, Y, $R_2$, or $R_3$ is other than hydrogen.

In the more preferred novel compounds of this invention,
X and Y are hydrogen,
R $\alpha$ ' is hydrogen,
R $\alpha$ is methyl or hydrogen,
$R_2$ and $R_3$ are each hydrogen or halogen, such as fluoro and chloro;
$R_4$ is COOH, with the proviso that if R $\alpha$ is hydrogen, then $R_2$ and $R_3$ are not both hydrogen.

Of particular interest are those compounds of the formula:

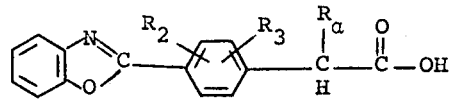

wherein $R_2$ and $R_3$ are each hydrogen, fluoro, or chloro (preferably fluoro) and R $\alpha$ is hydrogen or methyl; with the proviso that when R $\alpha$ is hydrogen, at least one R must be fluorine.

Specific members of this class which are highly effective antiinflammatory and antithrombotic agents include
4-(benzoxazol-2-yl)-2-fluorophenylacetic acid,
4-(benzoxazol-2-yl)-3-fluorophenylacetic acid,
2-[4-(benzoxazol-2-yl)-3-fluorophenyl]propionic acid,
2-[4-(benzoxazol-2-yl)phenyl]propionic acid.

With regard to the latter two compounds, in addition to the racemate and levo isomer, of interest is the "d" (dextro) isomer; (d)-2-[4-(benzoxazol-2-yl)phenyl]-propionic acid; (d)-2-[4-(benzoxazol-2-yl)-3-fluorophenyl]-propionic acid.

In addition to the above, representative compounds that may be employed in the practice of the invention include:
4-(benzoxazol-2-yl) 2,3-difluorophenylacetic acid,
4-(benzoxazol-2-yl) 2,5-difluorophenylacetic acid,
4-(benzoxazol-2-yl)-2-chlorophenylacetic acid, 4-(benzoxazol-2-yl) 5-chloro-2-fluorophenylacetic acid,
2-[4-(benzoxazol-2-yl)-3-chlorophenyl]propionic acid,
2-[4-(benzoxazol-2-yl)-2-fluorophenyl]propionic acid,
2-[4-(benzoxazol-2-yl)-2,3-difluorophenyl]propionic acid,
2-[4-(benzoxazol-2-yl)-2,5-difluorophenyl]propionic acid.

It should be noted that in addition to the free acids, encompassed within the scope of the preferred aspects of the invention are the corresponding alcohols, esters, amides and pharmaceutically acceptable addition salts.

The term "pharmaceutically acceptable addition salts" signifies those salts derived from pharmacologically acceptable inorganic and organic bases. Suitable salts include those of alkali metals such as sodium, potassium or lithium, those of alkaline earth metals such as magnesium and calcium, ammonium and salts of organic amines such as ethylamine, triethylamine, ethanolamine, diethanolamine, diethylaminoethanol, ethylenediamine, benzylamine, procaine, pyrrolidine, piperidine, morpholine, 1-ethyl-piperidine, 2-piperidinoethanol, dibenzylethylenediamine, and the like.

It should be understood, however, that the particular compound of Formula I when X, Y, $R_\alpha$, $R_\alpha'$, $R_2$ and $R_3$ are hydrogen and $R_4$ is COOH all at the same time thus forming 4-(benzoxazoyl-2-yl)phenylacetic acid is not included as a novel compound in this invention. The use of the above-mentioned specific compound as an antiinflammatory and antithrombotic agent should, however, be considered part of this invention.

The benzoxazoles of the invention possess a high degree of antiinflammatory, analgesic and antipyretic activity. They are of value in the treatment of arthritic and dermatological disorders or like conditions responsive to antiinflammatory drugs. In general they are indicated for a wide variety of conditions where one or more of the symptoms of inflammation, fever and pain are manifested. Included within this category are diseases such as rheumatoid arthritis, osteoarthritis, gout, infectious arthritis, rheumatic fever and inflammatory conditions of the ocular system. As indicated above the compounds utilized in the practice of the invention also possess a useful degree of analgesic and antipyretic activity.

The compounds of this invention also possess a high degree of activity as platelet aggregation inhibitors and are thus useful in the prevention of arterial thrombosis and related conditions.

For these purposes the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be, for example, inert diluents, such as lactose, calcium phosphate or sodium phosphate; granulating and disintegrating agents, for example, maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectibles.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc... containing the antiinflammatory agents are employed.

Dosage levels of the order of .5 mg. to 140 mg. per kilogram of body weight per day are useful in the treatment of the above indicated conditions ( 25 mg. – 7 gm. per patient per day). For example, inflammation, fever, pain and abnormal platelet aggregation, are effectively treated by the administration of about 0.1 to 50 mg. of the compound per kilogram of body weight per day (5 mg. to 3.5 gm. per patient per day). Advantageously, from about 1 mg. to about 15 mg. per kilogram of body weight per daily dosage produces highly effective results (50 mgs. to 1 gm. per patient per day).

The amount of active ingredient that may be combined with the carrier materials to produce a single dosage form will vary depending upon the host treated and the particular mode of administration. For example a formulation intended for the oral administration of humans may contain from 5 mg. to 5 gm. of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The novel compounds of this invention may be prepared as shown by the following schematic I:

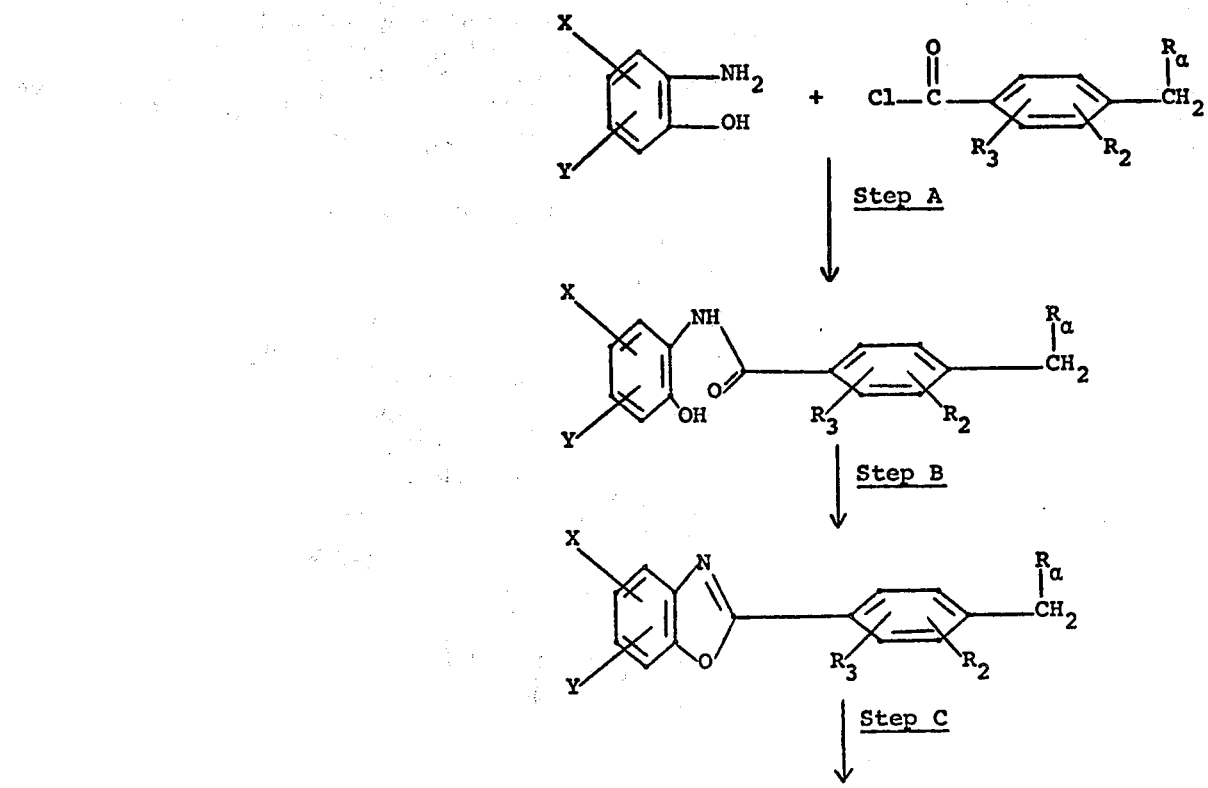

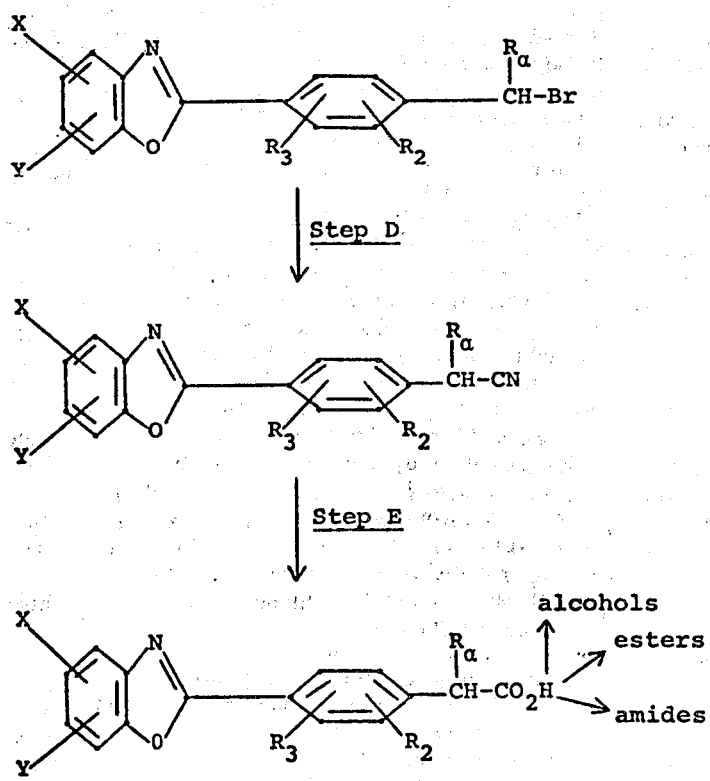

where X, Y, $R_2$, $R_3$ and $R\alpha$ are as previously defined.

Following is a particular description of each of the steps above:

Step A — Reaction of an appropriate o-aminophenol with an appropriate benzoic acid halide in pyridine at ambient temperature for 1–12 hours to yield the corresponding amide.

Step B — Heating the amide formed in Step A above its melting point at a temperature high enough to bring about ring closure to the benzoxazole - a temperature of 240° – 250°C. for 1 hour is usually sufficient.

Step C — Treatment of the alkylphenyl benzoxazole formed in Step B with N-bromosuccinimide in refluxing carbon tetrachloride preferably in the presence of a catalytic amount of dibenzoyl peroxide to give the corresponding bromo-alkylphenyl benzoxazole.

Step D — Treatment of the bromoalkylphenyl benzoxazole formed in Step C with sodium cyanide in methanol or DMSO at 60° – 70°C. for 1–3 hours to give the corresponding cyanoalkylphenyl benzoxazole.

Step E — Acid hydrolysis of the cyanoalkylphenyl benzoxazole formed in Step D by heating for 1 hour at 85° – 95°C. in concentrated hydrochloric acid to give the desired benzoxazole phenyl acetic acid.

Compounds which have an alkylidene linkage, particularly a methylene linkage, at the α-position of the acid side chain can be prepared according to the following process. Details of the process are shown in Example 8.

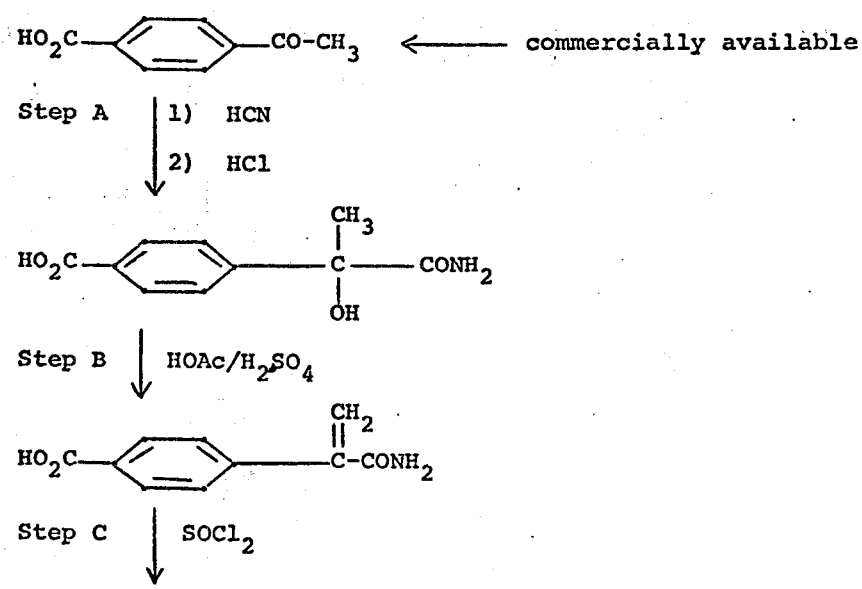

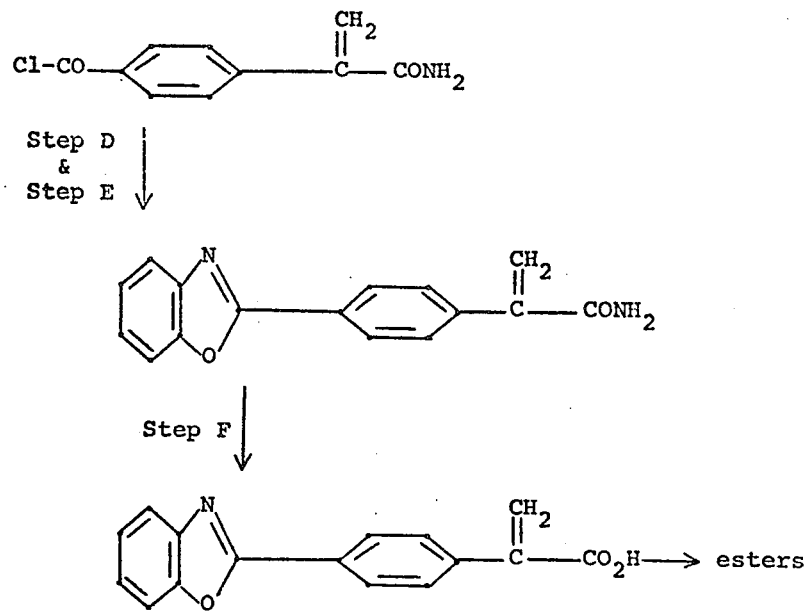

Step D
&
Step E

Step F

→ esters

Also, compounds of Formula I shown below where R α ' can be a methylene linkage attached to the unsubstituted ortho position of the benzenoid ring, can be prepared according to the initial Flow Sheet by replacing the alkylbenzoic acid with benzocyclobutene-4-carboxylic acid.

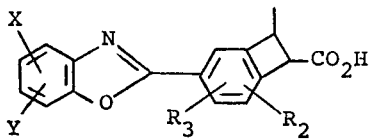

wherein X, Y, $R_2$ and $R_3$ are as previously defined.

The non-toxic salts of the acid can be prepared from the acid by any of the well known metathesis procedures. For example, the acid can be reacted with an inorganic base such as sodium hydroxide, potassium hydroxide, ammonium hydroxide, barium hydroxide, and the like.

The compounds of this invention, wherein $R_4$ is a group such that an ester is the final compound (i.e. $R_4$=alkoxycarbonyl), are prepared by any esterification procedure using an esterifying agent containing the appropriate $R_4$ group. For example, the acetic acid compounds of this invention may be reacted with the appropriate lower alkanol (preferably methanol) in the presence of a strong acid, such as hydrochloric acid, sulfuric acid, p-toluene-sulfonic acid, and the like, to form the desired $R_4$ compound. The methyl ester ($R_4$ = methoxycarbonyl) can also be prepared by the treatment of the acid with diazomethane.

The compounds of this invention, wherein $R_4$ is a group such that an amide is the final compound (i.e. $R_4$ is aminocarbonyl), may be prepared by any suitable amidation reaction. For example, the acetic acid compound (preferably the methyl or ethyl ester) may be reacted with ammonia, ammonium hydroxide, or an amine compound, at any suitable temperature (room temperature to reflux). When the amino group is desired, it is preferred to carry out the reaction with ammonia in a bomb at temperatures above 100°C. to form the desired $R_4$ amide compound.

The alcohols may be formed from the corresponding acids using reductive techniques well known to the art.

Members of this class include:
4-(benzoxazol-2-yl)-2-fluorophenylethanol,
4-(benzoxazol-2-yl)-3-fluorophenylethanol,
2-[4-(benzoxazol-2-yl)-3-fluorophenyl]propanol,
2-[4-(benzoxazol-2-yl)phenyl]propanol.

The following examples are used by way of illustration and should not be construed as limitations of the application.

EXAMPLE 1

4-(Benzoxazol-2-yl)-2-Fluorophenylacetic Acid

2'-Hydroxy-3-fluoro-p-toluanilide

To a solution of 4.5 gm. of o-aminophenol in 50 ml. of dry pyridine is added a solution of 3-fluoro-p-toluyl chloride (prepared from 5 gm. of 3-fluoro-p-toluic acid and thionyl chloride) in 10 ml. of benzene. An exothermic reaction takes place and the reaction mixture is stirred overnight at ambient temperature. The reaction mixture is concentrated in vacuo and taken up between 2.5 N hydrochloric acid and chloroform. The organic layer is separated, dried over sodium sulfate and concentrated to dryness. The residue is recrystallized from methanol to yield 2'-hydroxy-3-fluoro-p-toluanilide, m.p. 195°–197°C.

When benzocyclobutene-4-carbonyl chloride is used in place of 3-fluoro-p-toluyl chloride in the above example, there is obtained N-(2-hydroxyphenyl)benzocyclobutene-4-carboxamide.

When 2-amino-6-chlorophenol and 2-amino-4,6-dichlorophenol are used in place of o-aminophenol and when p-toluyl chloride is used in place of 3-fluoro-p-toluyl chloride in the above example, there is obtained 3'-chloro-2'-hydroxy-p-toluanilide and 3',5'-dichloro-2'-hydroxy-p-toluanilide, respectively.

B. 2-(3-Fluoro-4-methylphenyl)benzoxazole

2'-Hydroxy-3-fluoro-p-toluanilide (7.0 gm.) is heated in a wood's metal bath for 1 hour at 225°–245°C. The reaction mixture is then cooled, taken up in a mixture of etherbenzene (11) and washed successively with 2.5 N NaOH and water. The organic phase is separated, dried over sodium sulfate and concentrated. Chromatography on 200 gm. of silica gel and elution with ether in hexane (0–2%) gives 2-(3-fluoro-4-methylphenyl)benzoxazole, m.p. 121°–122°C.

When 3'-chloro-2'-hydroxy-p-toluanilide, 3',5'- dichloro-2′-hydroxy-p-toluamide, and N-(2-hydroxyphenyl)-benzocyclobutene-4-carboxamide are used in place of 2′-hydroxy-3-fluoro-p-toluanilide in the above example, there is obtained 7-chloro-2-(4-methylphenyl)benzoxazole, 5,7-dichloro-2-(4-methylphenyl)-benzoxazole, and 4-(benzoxazol-2-yl)benzocyclobutene, respectively.

C. 2-(4-Bromomethyl-3-fluorophenyl)benzoxazole

To a solution of 5.1 gm. of 2-(3-fluoro-4-methyl-phenyl) benzoxazole in 60 ml. of carbon tetrachloride is added 6.23 gm. N-bromosuccinimide and 100 mg. of dibenzoyl peroxide. The reaction mixture is refluxed for 6 hours, filtered to remove succinimide and the filtrate concentrated to dryness. The residue is chromatographed on 500 gm. of silica gel. Elution with 1% ether in petroleum ether gives 2-(4-bromomethyl-3-fluorophenyl)benzoxazole, m.p. 150°–152°C.

When 7-chloro-2-(4-methylphenyl)benzoxazole, 5,7-dichloro-2-(4-methylphenyl)benzoxazole and 4-benzoxazol-2-yl)benzocyclobutene are used in place of 2-(3-fluoro-4-methylphenyl)benzoxazole in the above example, there is obtained 7-chloro-2-(4-bromomethylphenyl)benzoxazole, 5,7-dichloro-2-(4-bromomethylphenyl)benzoxazole, and 4-(benzoxazol-2-yl)-1-bromobenzocyclobutene, respectively.

D. 4-(Benzoxazol-2-yl)-2-fluorophenyl acetonitrile

To a solution of 0.6 gm. of sodium cyanide in 25 ml. of dimethyl sulfoxide preheated to 65°–70°C. is slowly added 2.5 gm. of 2-(4-bromomethyl-3-fluorophenyl)-benzoxazole. The reaction mixture is heated at 60°–70°C. for 1 hour, then cooled and poured into water. The resulting precipitate is filtered off and chromatographed on 300 gm. of silica gel. Elution with methylene chloride gives 4-(benzoxazol-2-yl)-2-fluorophenylacetonitrile.

When 7-chloro-2-(4-bromomethylphenyl)benzoxazole, 5,7-dichloro-2-(4-bromomethylphenyl)benzoxazole and 4-(benzoxazole-2-yl)-1-bromobenzocyclobutene are used in place of 2-(4-bromomethyl-3-fluorophenyl)benzoxazole in the above example, there is obtained 4-(7-chlorobenzoxazol-2-yl)-phenylacetonitrile, 4-(5,7-dichlorobenzoxazol-2-yl)phenyl-acetonitrile, and 4-(benzoxazol-2-yl)-1-cyanobenzocyclobutene, respectively.

E. 4-(Benzoxazol-2-yl)-2-fluorophenylacetic acid

A solution of 2.0 gm. of 4-(benzoxazol-2-yl)-2-fluorophenylacetonitrile in 30 ml. of concentrated hydrochloric acid is heated on a steam-bath for 1 hour. The reaction mixture is then filtered through a sintered glass filter into 200 ml. of water. The precipitate which forms is collected by filtration and air dried. Recrystallization from ethanol gives 4-(benzoxazol-2-yl)-2-fluorophenylacetic acid, m.p. 213°–216°C.

When 4-(7-chlorobenzoxazolyl-2-yl)phenylacetonitrile, 4-(5,7-dichlorobenzoxazol-2-yl)phenylacetonitrile and 4-(benzoxazol-2-yl)-1-cyanobenzocyclobutene are used in place of 4-(benzoxazol-2-yl)-2-fluorophenylacetonitrile in the above example, there is obtained 4-(7-chlorobenzoxazol-2-yl)phenylacetic acid, m.p. 225°–229°C. 4-(5,7-dichloro-benzoxazol-2-yl)phenylacetic acid, m.p. 205°–210°C., and 4-(benzoxazol-2-yl)benzocyclobutene-1-carboxylic acid, respectively.

EXAMPLE 2

4-(Benzoxazol-2-yl)-3-fluorophenylacetic acid

A. 2′-Hydroxy-2-fluoro-p-toluanilide

To a solution of 3.3 gm. o-aminophenol in 50 cc. of dry pyridine is added a solution of 4 gm. of 2-fluoro-p-toluyl chloride (prepared from 3.3 gm. of 2-fluoro-p-toluic acid and 25 cc. of thionyl chloride) in 25 ml. of benzene. An exothermic reaction takes place and the reaction mixture is stirred overnight at ambient temperature. The reaction mixture is concentrated in vacuo and taken up between 2.5 N hydrochloric acid and a 1:1 mixture of chloroform-methylene chloride. The organic layer is separated and washed with a saturated $NaHCO_3$ solution then with water. Concentration in vacuo followed by recrystallization from methanol gives 2′-hydroxy-2-fluoro-p-toluanilide, m.p. 181°–183°C.

B. 2-(2-Fluoro-4-methylphenyl)benzoxazole

2′-Hydroxy-2-fluoro-p-toluanilide (3.5 gm.) is heated for 1 hour in a Wood's metal bath which had been preheated to 250°C. The reaction mixture is cooled, taken up in chloroform, washed with dilute sodium hydroxide and water. The organic phase is dried over sodium sulfate and concentrated in vacuo to give 2.7 gm. of crude product. Chromatography on 500 gm. of silica gel and elution with methylene chloride gives pure 2-(2-fluoro-4-methylphenyl)-benzoxazole, m.p. 115°–117°C.

C. 2-(4-Bromomethyl-2-fluorophenyl)benzoxazole

To a solution of 5.0 gm. of 2-(2-fluoro-4-methylphenyl)benzoxazole in 200 cc. of carbon tetrachloride is added 4.5 gm. of N-bromosuccinimide and 50 mg. of dibenzoyl peroxide. The mixture is refluxed for 2 hours, filtered to remove succinimide and concentrated in vacuo. The residue is recrystallized from toluene to give 2-(4-bromomethyl-2-fluorophenyl)benzoxazole, m.p. 170°–173°C.

D. 4-(Benzoxazol-2-yl)-3-fluorophenylacetonitrile

To a mixture of 1.0 gm. of 2-(4-bromomethyl-2-fluorophenyl)benzoxazole in 50 cc. of dry methanol which has been cooled in an ice-water bath is added 1.5 gm. of sodium cyanide. The reaction mixture is stirred cold for 10 minutes, allowed to warm to room temperature and finally heated on the steam bath. Solution of the starting material occurs and after 5 minutes reflux the reaction mixture is cooled, concentrated to about 25 cc., and poured into 100 cc. of ice cold 2.5 N hydrochloric acid. The resulting precipitate is filtered and air dried to give crude 4-(benzoxazol-2-yl)-3-fluorophenylacetonitrile.

E. 4-(Benzoxazol-2-yl)-3-fluorophenylacetic acid

A mixture of 0.7 gm. of the above crude 4-(benzoxazol-2-yl)-3-fluorophenylacetonitrile and 30 cc. of concentrated hydrochloric acid is heated on the steam bath for 1 hour. The reaction mixture is then filtered through a sintered glass filter into ice water and the resulting precipitate collected to give 0.65 gm. of crude product. The crude acid is stirred with 50–60 cc. of saturated sodium bicarbonate solution, a small amount of charcoal is added, and the mixture is then filtered. The filtrate is acidified with concentrated hydrochloric acid and the resulting precipitate collected and dried to give 4-(benzoxazol-2-yl)-3-fluorophenylacetic acid, m.p. 207°–211°C. dec.

EXAMPLE 3

2[4-(Benzoxazol-2-yl)-3-fluorophenyl]propionic acid

A. Ethyl 2-amino- 4-ethylbenzoate

A mixture of 59.4 gm. of 4-ethylanthranilic acid and 1,000 cc. of ethanol is saturated with dry hydrogen chloride gas and then refluxed overnight. The reaction mixture is then concentrated in vacuo and the residue taken up between ether and sodium bicarbonate solution. The ether extract is dried and concentrated in vacuo to give ethyl 2-amino-4-ethylbenzoate as an oil (characterized by IR and NMR).

B. Ethyl 4-ethyl-2-fluorobenzoate

To a slurry of 44 gm. of ethyl 2-amino-4-ethyl benzoate, 150 cc. of concentrated hydrochloric acid and 150 cc. of water, which has been cooled to 0° to −5°, is slowly added a solution of 27.6 gm. of sodium nitrite in 50 cc. of water. The reaction mixure is stirred in the cold until solution occurs and then 70 gm. of fluoboric acid (48%) is added. The diazonium fluoborate precipitates and is collected by filtration and air dried to give 15.9 gm. of material. The filtrate is concentrated in vacuo at low temperature to give crude diazonium salt. Decomposition of the above diazonium fluoborates at 150° gives crude ethyl 4-ethyl-2-fluorobenzoate as an oil.

C. 4-Ethyl-2-fluorobenzoic acid

A mixture of 22.8 gm of ethyl 4-ethyl-2-fluoro benzoate, 200 cc. of ethanol and 100 ml. of 2.5 N sodium hydroxide is heated at 60° for 4 hours and then concentrated in vacuo. The residue is taken up in water, filtered and the filtrate acidified with concentrated hydrochloric acid. The precipitate is collected and air dried to give 4-ethyl-2-fluorobenzoic acid.

D. 4-Ethyl-2-fluoro-2'-hydroxybenzanilide

To a solution of 13.08 gm. of o-aminophenol in 150 cc. of dry pyridine which is cooled in ice water is added a solution of 4-ethyl-2-fluorobenzoyl chloride (prepared from 20.0 gm. of acid and thionyl chloride) in 30 cc. of dry benzene. The mixture is stirred at room temperature overnight and then concentrated in vacuo. The residue is treated with water and the precipitate collected by filtration to give crude 4-ethyl-2-fluoro-2'-hydroxybenzanilide which was characterized by infra red spectra then used in the following step.

E. 2-(4-Ethyl-2-fluorophenyl)benzoxazole

4-Ethyl-2-fluoro-2'-hydroxybenzanilide (29.0 gm.) is heated for 40 minutes in a Wood's metal bath at 240°C. The reaction mixture is then cooled, taken up in chloroform and the chloroform solution treated with carbon, dried over magnesium sulfate and concentrated in vacuo to give 2-(4-ethyl-2-fluorophenyl)benzoxazole.

F. 2-[4-(1-bromoethyl)-2-fluorophenyl]benzoxazole

A mixture of 26 gm. 2l -(4-ethyl-2-fluorophenyl) benzoxazole, 19.76 gm. of N-bromosuccinimide and 50 mg. of dibenzoyl peroxide in 150 cc. of carbon tetrachloride is refluxed until the N-bromosuccinimide is consumed. The reaction mixture is filtered and the filtrate concentrated to give 2-[4-(1-bromoethyl)-2-fluorophenyl]benzoxazole, m.p., 103°–104°C.

G. 2-[4-(benzoxazole-2-yl)-3-fluorophenyl]propionitrile

A mixture of 16 gm. 2-[4-(1-bromoethyl)- 2-fluorophenyl]benzoxazole, 17 gm. sodium cyanide and 150 cc. of dry methanol are heated on the steam bath for about 2 hours. The reaction mixture is cooled, poured into ice-water containing 25 cc. of concentrated hydrochloric acid and the resulting mixture is extracted well with chloroform. The combined chloroform extracts are washed with water, dried and concentrated in vacuo. The crude product (14 gm.) is chromatographed on 1000 gm. of silica gel. Elution with methylene chloride gives 2-[4-(benzoxazol-2-yl)-3-fluorophenyl]propionitrile.

H. 2-[4-(benzoxazol-2-yl)-3-fluorophenyl]propionic acid

A mixture of 3.1 gm. of 2-[4-(benzoxazol-2-yl)-3-fluorophenyl]propionitrile and 25 cc. of concentrated hydrochloric acid is heated at 90°C. for 1½ hours. The reaction mixture is poured into ice water and extracted well with ether. The combined ether extracts are washed with water, dried over sodium sulfate and concentrated in vacuo to yield 2-[4-(benzoxazol-)2-yl)-3-fluorophenyl]propionic acid, m.p. 168–171°C.

Employing the procedures substantially as described in Examples 1, 2, or 3 (Steps D to H) and as outlined by Reaction Scheme I, but substituting for the particular o-aminophenol and 4-alkylbenzoic acid used therein, the various known o-aminophenols and 4-alkylbenzoic acids identified in Table I, there are produced the substituted 4-(benzoxazol-2-yl)phenylacetic acids also identified in Table I.

TABLE I

| X | Y | $R_2$ | $R_3$ | $R_\alpha$ |
|---|---|---|---|---|
| H | H | 2-F | 3-F | H |
| H | H | 2-F | 5-F | H |
| H | H | 2-Cl | H | H |
| H | H | 2-F | 5-Cl | H |
| 4-t-$C_4H_9$- | H | H | H | H |
| 5-$C_2H_5$ | H | H | 6-$NO_2$- | H |
| 5-i-$C_3H_7$- | 7-i-$C_3H_7$- | H | H | H |
| 5-$CH_3O$- | H | H | H | H |
| 5-HO- | H | H | H | H |
| 6-F- | H | H | 6-$(CH_3)_2M$- | H |
| 5-$CH_3SO_2$- | 7-Cl- | H | H | H |
| H | 6-$NO_2$- | H | H | H |
| H | 6-$(CH_3)_2N$- | H | H | H |
| 5-$(C_2H_5)_2N$- | H | H | H | H |
| H | 6-Br | 3-$NH_2$ | H | H |
| H | H | 3-$CH_3S$ | H | H |
| H | H | 2-Cl | 5-$NO_2$- | H |
| H | H | 2-$NO_2$- | 6-F- | H |
| H | H | 3-Br | H | H |
| H | H | 2-Cl | 5-Cl | H |
| H | H | 3-Cl | H | $CH_3$ |
| H | H | 2-F | H | $CH_3$ |
| H | H | 2-F | 3-F | $CH_3$ |
| H | H | 2-F | 5-F | $CH_3$ |

EXAMPLE 4

2-[4-(Benzoxazol-2-yl)phenyl]propionic Acid

A. 4-Ethyl-2'-hydroxybenzanilide

To a solution of 8.2 gm. of o-aminophenol in 70 cc. of dry pyridine is added a solution of p-ethylbenzoyl chloride (prepared from 10 gm. of p-ethylbenzoic acid and thionyl chloride) in 20 cc. of benzene. An exothermic reaction occurs and the reaction mixture is stirred overnight at ambient temperature. The mixture is concentrated in vacuo and taken up between a 1:1 mixture of benzene and ether and 2.5 N hydrochloric acid. The organic layer is washed with saturated sodium bicarboxate, water, then dried and concentrated. Recrystallization from benzene-hexane gives 4- ethyl-2'-hydroxybenzanilide, m.p. 103°–105°C.

B. 2-(4-Ethylphenyl)benzoxazole

4-Ethyl-2'-hydroxybenzanilide (10.2 gm.) is heated for 1 hour in a Wood's metal bath at 235°–245°C. The reaction mixture is cooled, taken up in ethanol-ether (1:1) and washed with dilute sodium hydroxide. The organic layer is washed with water, dried over sodium sulfate and concentrated in vacuo. Chromatography on 500 gm. of silica gel and elution with ether in petroleum ether (1–2%) gives 2-(4-ethylphenyl)benzoxazole, m.p. 84°–86°C.

C. 2-(4-[1-bromoethyl]phenyl)benzoxazole

To a solution of 7.1 gm. of 2-(4-ethylphenyl) benzoxazole in 125 cc. of carbon tetrachloride is added 6.2 gm. of N-bromosuccinimide and 50 mg. of benzoyl peroxide. The mixture is refluxed for about one half hour at which time the N-bromosuccinimide was consumed. Filtration followed by concentration of the filtrate gives 2-(4-[1-bromoethyl]Phenyl)benzoxazole, m.p. 128°–131°C.

D. 2-(4-[Benzoxazol-2-yl]phenyl)propionitrile

To a solution of 2.45 gm. of sodium cyanide in 100 cc. of dimethyl sulfoxide heated to 70°C. in an oil bath is added 10.0 gm. of 2-(4-[1-bromoethyl]phenyl) benzoxazole. The reaction mixture is heated at 65°–75°C. for 1½ hours during which time it turns red-brown in color. The reaction mixture is poured into ice water and extracted well with methylene chloride. The combined methylene chloride extracts are washed well with water, dried and concentrated to give crude product. Chromatography of the crude material on 400 gm. of silica gel and elution with methylene chloride gives pure 2-(4-[benzoxazol-2-yl]phenyl) propionitrile, m.p. 116°–117°C. (methylene-chloride-hexane).

E. 2-(4-[Benzoxazol-2-yl]phenyl)propionic Acid

A mixture of 1.8 gm. of 2-(4-[benzoxazol-2-yl]phenyl)propionitrile and 20 cc. of concentrated hydrochloric acid is heated on the steam bath for 1 hour. The mixture is then filtered through sintered glass into 200 cc. of ice water and the resulting precipitate is filtered and air dried to give the crude product. Recrystallization from methanol gives 2-(4-[benzoxazol-2-yl]phenyl)propionic acid, m.p. 174°–178°C.

EXAMPLE 5

Resolution of 2-(4-[Benzoxazol-2-yl]phenyl)propionic Acid

A. l-isomer

To a solution of 3.0 gm. of 2-(4-[benzoxazol-2-yl]phenyl)propionic acid in 200 cc. of ether-methylene chloride (1:1) is added 3.0 ml. of (−)-α-methylbenzylamine. The resulting salt precipitates and is collected by filtration to give 4.0 gm. of the amine salt of the acid. Repeated recrystallization from acetone (5 times from 100–150 cc. acetone) gives 0.666 gm. of salt which when dissolved in methanol-water and treated with concentrated hydrochloric acid gives 1-2-(4-[benzoxazol-2-yl]phenyl)propionic acid, m.p. 175°–177°C. $[\alpha]_D = -45.1 \pm 0.8°$.

B. d-isomer

A mixture of 2.0 gm of d-enriched 2-(4-[benzoxazol-2-yl]phenyl)propionic acid recovered from the mother liquors of the above recrystallizations and 2.5 gm. of the cinchonidine is heated in 500 cc. of chloroform until solution occurs and is then concentrated in vacuo to give a yellow white solid. Repeated recrystallization from acetone (5X) gives 1.6 gm. of salt which when taken up between benzene-ether and dilute hydrochloric acid yields from the organic layer d-2-(4-[benzoxazol-2-yl]phenyl) propionic acid. Recrystallization from methanol-water gives the pure product, m.p. 175°–178°C. $[\alpha]_D = +44.2 \pm 0°$.

Since the α-methyl phenylacetic acid compounds of this invention possess asymmetric carbon atoms, they are ordinarily present in the form of a racemic mixture. The resolution of such racemates can be carried out by a vast number of known methods. Thus, some racemic mixtures can be precipitated as eutectics instead of mixed crystals and can thus be quickly separated and in such cases can sometimes be selectively precipitated. The more common method of chemical resolution may be used. By this method diastereomers are formed from the racemic mixture by reaction with an optically-active resolving agent. Thus, an optically-active base can be reacted with the carboxyl group. The difference in solubility between the diastereomers formed permits the selective crystallization of one form and regeneration of the optically-active acid from the mixture. There is, however, a third method of resolving which shows great promise. This involves biochemical procedures using selective enzymatic reaction. Thus, the racemic acid can be subjected to an asymmetric oxidase or decarboxylase which will, by oxidation or decarboxylation, destroy one form, leaving the other form unchanged. Of interest is the use of a hydrolysase on a derivative of the racemic mixture to form preferentially one form of the acid. Thus, ester or amides of the acids can be subjected to an esterase which will selectively saponify one enantiomorph and leave the other unchanged.

Furthermore, it should be noted that the above resolution methods may be employed at any stage of the synthesis upon such intermediates that have an asymmetric carbon atom.

As indicated previously, of particular interest are the (d) isomer of 2-[4-(benzoxazol-2-yl)phenyl]propionic acid and 2-[4-(benzoxazol-2-yl)-3-fluorophenyl]propionic acid. The desired (d) isomer of the free acid may be prepared by any one of the preceding described resolving methods, preferably working from the free acid as the starting material. For example, amide or salt diastereomers of the free acid may be formed with optically-active amines, such as quinine, brucine, cinchonidine, cinchonine, hydroxyhydrindamine, methylamine, morphine, α-phenylethylamine, phenyloxynaphthylmethylamine, quinidine, 1 -fenchylamine, strychnine, basic amino acids, such as lysine, arginine, amino acid esters, and the like. Similarly, ester diastereomers of the free acid may be formed with optically-active alcohols, such as borneol, menthol, 2-octanol and the like. Especially preferred is the use of cinchonidine to give the readily decomposable diastereomer salt which may then be resolved by dissolving in a solvent, such as acetone, and distilling the solvent at atmospheric pressure until crystals begin to appear and further crystallization produced by allowing the mixture to cool to room temperature, thereby separating the two enantiomorphs. The (d) acid may then be recovered from the (d) salt by extracting the salt between an inorganic solvent, such as ether and dilute hydrochloric acid.

In summary, resolution of the acid into the "d" and "l" forms may be accomplished using techniques well known to the art. See for example "Stereochemistry of Carbon Compounds", E. L. Eliel, McGraw Hill (1962), pages 47–85, which reveals methods of resolution which may be used in the practice of the invention and are incorporated herein by reference. Illustrative of such methods are the following:

a. Resolution by mechanical separation of crystals.
b. Resolution by formation of diastereoisomers.
c. Resolution by equilibrium asymmetric transformation.
d. Resolution by kinetic asymmetric transformation.
e. Biochemical asymmetric transformation.
f. Absolute asymmetric synthesis.
g. Asymmetric synthesis involving symmetric compounds.

EXAMPLE 6

Methyl 4-(benzoxazol-2-yl)phenylacetate

To a solution of diazomethane in 75 ml. of ether is added, portionwise, as a solid, 1.0 gm. of 4-(benzoxazol-2-yl)phenylacetic acid. Nitrogen is evolved and after 1 hour the excess diazomethane is consumed by adding acetic acid. The reaction mixture is filtered and the filtrate concentrated to give a yellow solid. Recrystallization from methanol gives methyl 4-(benzoxazol-2-yl)phenylacetate, m.p. 109°–112°C.

As indicated previously, esters may be prepared using techniques well known to the art. For example, esters may be prepared from the corresponding acids, by conversion to the corresponding acid halides and treatment with the desired alcohol. Representative examples of esters that may be prepared using this procedure is as follows:

ethyl 4-(benzoxazol-2-yl)-2-fluorophenyl acetate
allyl 4-(benzoxazol-2-yl)-2-fluorophenyl acetate
ethynyl 4-(benzoxazol-2-yl)-2-fluorophenyl acetate
cyclopropyl 4-(benzoxazol-2-yl)-2-fluorophenyl acetate
phenyl 4-(benzoxazol-2-yl)-2-fluorophenyl acetate
o-tolyl 4-(benzoxazol-2-yl)-2-fluorophenyl acetate
p-carboxyphenyl 4-(benzoxazol-2-yl)-3-fluorophenyl acetate
o-carboxamidophenyl 4-(benzoxazol-2-yl)-3-fluorophenyl acetate
methoxymethyl 4-(benzoxazol-2-yl)-3-fluorophenyl acetate
hydroxymethyl 2-[4-(benzoxazol-2-yl)-3-fluorophenyl]propionate
dimethylaminomethyl 2-[4-(benzoxazol-2-yl)-3-fluorophenyl]-propionate
α-tetrahydropyranyl d-2-[4-(benzoxazol-2-yl)phenyl]-propionate.

EXAMPLE 7

4-(Benzoxazol-2-yl)phenylacetamide

A solution of 0.1 gm. of 4-(benzoxazol-2-yl)-phenylacetonitrile in 2 ml. of concentrated hydrochloric acid is allowed to stand at room temperature overnight. The reaction mixture is then filtered through a sintered glass filter into 50 ml. of cold water. The resulting precipitate is collected and air dried to give 4-(benzoxazol-2-yl)-phenylacetamide, m.p. 251°–255°C.

The amides of the invention may be conveniently prepared using conventional techniques well known to the art. For example, the amides may be prepared from the corresponding acids by conversion to the corresponding acid halides and treatment with the desired amine. Representative members of amides include the following:

N-methyl 4-(benzoxazol-2-yl)phenylacetamide
N-hydroxmethyl 4-(benzoxazol-2-yl)phenylacetamide
N,N-di(hydroxymethyl) 4-(benzoxazol-2-yl)phenylacetamide
N-dihydroxymethyl 4-(benzoxazol-2-yl)phenylacetamide
N-phenylmethyl 4-(benzoxazol-2-yl) 3-fluorophenylacetamide
N-phenyl 4-(benzoxazol-2-yl) 3-fluorophenylacetamide
N-m-hydroxyphenyl 4-(benzoxazol-2-yl) 3-fluorophenyl-acetamide
N-o-hydroxyphenyl-2-[4-(benzoxazol-2-yl) 3-fluorophenyl]-propionamide
N,N-dimethyl 2-[4-(benzoxazol-2-yl) 3-fluorophenyl]-propionamide
N-cyclohexyl 2-[4-(benzoxazol-2-yl) 3-fluorophenyl]-propionamide
N-carboxymethyl 4-(benzoxazol-2-yl)-2-fluorophenylacetamide
N,N-diphenyl 4-(2-benzoxazolyl)-2-fluorophenylacetamide
N-hydroxymethyl-d-2 [4-benzoxazol-2-yl)phenyl]propionamide.

EXAMPLE 8 p-(Benzoxazol-2-yl)atropic Acid

A. p-Carboxy-α-hydroxyhydratropamide 0.1 Moles of p-acetylbenzoic acid and 30 ml. of liquid hydrogen cyanide are stirred at 0°C. for 5 minutes. There is then added 5 ml. of piperidine and the resulting mixture stirred at 0°C. for 1½ hours. The mixture is then poured into 250 ml. of concentrated hydrochloric acid (previously cooled to 0°C.), saturated with hydrogen chloride gas, stirred cold 1 hour, and then at room temperature over night. Extraction with chloroform, washing the chloroform extracts with water, drying and concentrating in vacuo, gives p-carboxy-α-hydroxyhydratropamide.

B. p-Carboxyatropamide

To a solution of 0.05 moles of p-carboxy-α-hydroxyhydratropamide in 50 cc. of acetic acid is added 5 cc. of a concentrated sulfuric acid. The mixture is heated on the steam-bath for ½ hour, then concentrated in vacuo. Addition of water to the residue and filtration gives p-carboxyatropamide.

C. p-Chlorocarbonylatropamide

A mixture of 50 cc. of thionyl chloride and 0.05 moles of p-carboxyatropamide is heated at reflux on the steam-bath for ½ hour. The reaction mixture is concentrated in vacuo to give p-chlorocarbonylatropamide suitable for use in the following step.

D. 4-(1-Carboxamidovinyl)-2′-hydroxybenzanilide

When p-chlorocarbonylatrophamide is used in place of 3-fluoro-p-toluyl chloride in the procedure of Example IA, there is obtained 4-(1-carboxamidovinyl)-2′-hydroxy-benzanilide.

E. p-(Benzoxazol-2-yl)atropamide

When 4-(1-carboxamidovinyl)-2′-hydroxybenzanilide is used in place of 2′-hydroxy-3-fluoro-p-toluanilide in the procedure of Example 1B, there is obtained p-(benzoxazol-2-yl)atropamide.

F. p-(Benzoxazol-2-yl)atropic Acid

A mixture of 0.01 mole of p-(benzoxazol-2-yl)-atropamide, 15 ml. of acetic acid and 15 ml. of concentrated hydrochloric acid is heated on the steam-bath for 1 hour. Filtration of the reaction mixture into 200 ml. of cold water, followed by filtration of the resulting precipitate, gives p-(benzoxazol-2-yl)atropic acid.

The following are illustrative of the techniques that may be employed in the preparation of pharmaceutical formulations to be utilized in the practice of the invention:

EXAMPLE 9

A mixture of 250 parts of 4-(benzoxazol-2-yl)-2-fluorophenyl acetic acid and 25 parts of lactose is granulated with suitable water, and to this is added 100 parts of maize starch. The mass is passed through a 16 mesh screen. The granules are dried at a temperature below 60°C. The dry granules are passed through a 16 mesh screen, and mixed with 3.8 parts of magnesium stearate. They are then compressed into tablets suitable for oral administration.

The specific benzoxazole used in the foregoing example may be replaced by 25, 100, 250, or 500 parts of other benzoxazoles of this invention to produce tablets suitable for oral administration as an antiinflammatory, antipyretic and/or analgesic according to the method of this invention.

EXAMPLE 10

A mixture of 50 parts of 4-(benzoxazol-2-yl)-3-fluorophenyl acetic acid, 3 parts of the calcium salt of lignin sulphonic acid, and 237 parts of water is ball-milled until the size of substantially all of the particles of the acid is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

EXAMPLE 11

A mixture of 250 parts of d-4-(benzoxazol-2-yl)-α-methylphenyl acetic acid, 200 parts of maize starch and 30 parts of alginic acid is mixed with a sufficient quantity of 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 12

A mixture of 500 parts 4-(benzoxazol-2-yl)-3-fluoro-α-methylphenyl acetic acid, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 13

1. Tablets — 10,000 scored tablets for oral use, each containing 500 mg. of active ingredient, are prepared from the following ingredients:

|  | Gm. |
|---|---|
| 4-(benzoxazol-2-yl)-2-fluorophenyl acetic acid | 5000 |
| Starch, U.S.P. | 350 |
| Talc, U.S.P. | 250 |
| Calcium stearate | 35 |

The powdered phenylacetic acid is granulated with a 4% w./v. aqueous solution of methylcellulose U.S.P. (1500 cps.). To the dried granules is added a mixture of the remainder of the ingredients and the final mixture compressed into tablets of proper weight.

2. Capsules — 10,000 two-piece hard gelatine capsules for oral use, each containing 250 mg. of benzoxazole are prepared from the following ingredients:

|  | Gm. |
|---|---|
| (d) 4-(benzoxazol-2-yl)-α-methyl-phenylacetic acid | 2500 |
| Lactose, U.S.P. | 1000 |
| Starch, U.S.P. | 300 |
| Talc, U.S.P. | 65 |
| Calcium stearate | 25 |

The powdered benzoxazole is mixed with the starch-lactose mixture followed by the talc and calcium stearate. The final mixture is then encapsulated in the usual manner Capsules containing 10, 25, 50, and 100 mg. of benzoxazol are also prepared by substituting 100, 250, 500, and 1000 gm. for 2500 gm. in the above formulation.

3. Soft elastic capsules — One-piece soft elastic capsules for oral use, each containing 200 mg. of benzoxazole are prepared in the usual manner by first dispersing the powdered active material in sufficient corn oil to render the material capsulatable.

4. Aqueous suspension — An aqueous suspension for oral use containing in each 5 ml., 1 gram of benzoxazol is prepared from the following ingredients:

| | | |
|---|---|---|
| 4-(benzoxazol-2-yl)-3-fluoro-phenylacetic acid | gm. | 2000 |
| Methylparaben, U.S.P. | gm. | 7.5 |
| Propylparaben, U.S.P. | gm. | 2.5 |
| Saccharin sodium | gm. | 12.5 |
| Glycerin | ml. | 3000 |
| Tragacanth powder | gm. | 10 |
| Orange oil flavor | gm. | 10 |
| F.D. & C. orange dye | gm. | 7.5 |
| Deionized water, q.s. to 10,000 mg. | | |

What is claimed is:

1. A method for treating a condition exhibiting abnormal platelet aggregation which comprises the administration to humans and animals of a therapeutically effective amount of a compound having the formula:

[Structure diagram]

or a pharmaceutically acceptable salt thereof, wherein
$R_\alpha$ is hydrogen or methyl;
$R'_\alpha$ is hydrogen, or $R_\alpha$ and $R'_\alpha$ taken together can be methylene: of $R'_\alpha$ can be a methylene linkage attached to the unsubstituted ortho position of the benzenoid ring;
X, Y, $R_2$ and $R_3$ are the same or different and each is hydrogen, $C_{1-5}$alkyl, chloro, bromo, fluoro; and
$R_4$ is COOH; COOR, wherein R may be $C_{1-5}$alkyl, $CONH_2$, $$CON<^Y_Y, \quad CON<^Y_Y,$$

where Y may be $C_{1-3}$alkyl.

2. The method according to claim 1 wherein the compound has the formula:

[Structure diagram]

and pharmaceutically acceptable non-toxic addition salts thereof, wherein
$R_\alpha$ is hydrogen or methyl;
X Y, $R_2$ and $R_3$ are the same or different and each is hydrogen, $C_{1-5}$alkyl, chloro, bromo, fluoro, and
$R_4$ is COOH or COOR wherein R is $C_{1-5}$alkyl.

3. A method of treating a condition exhibiting abnormal platelet aggregation which comprises the administration to humans and animals of a therapeutically effective amount of a compound having the formula:

[Structure diagram]

or a pharmaceutically acceptable salt thereof, wherein
$R_\alpha$ is hydrogen or methyl;
$R_2, R_3$, X and Y are each hydrogen, chloro, bromo, or fluoro; and
$R_4$ is COOH;
COOR, where R may be $C_{1-5}$alkyl, $CONH_2$; or $$CON<^Y_Y, \quad CON<^Y_Y,$$

where Y may be $C_{1-3}$alkyl.

4. The method according to claim 3 wherein the compound has the formula:

[Structure diagram]

or pharmaceutically acceptable salt thereof, wherein
$R_2$ and $R_3$ are each hydrogen or fluoro;
$R_\alpha$ is hydrogen or methyl;
$R_4$ is COOH or COOR wherein R is $C_{1-5}$ alkyl.

5. The method according to claim 4 wherein the compound has the formula:

[Structure diagram]

or pharmaceutically acceptable salt thereof wherein $R_2$ and $R_3$ are each hydrogen or fluorine with at least one R being fluorine.

6. The method according to claim 4 wherein the compound has the formula:

[Structure diagram]

or pharmaceutically acceptable salt thereof wherein $R_2$ and $R_3$ are hydrogen or fluorine.

7. The method according to claim 5 employing 4-(benzoxzol-2-yl)-2-fluorophenylacetic acid or a pharmaceutically acceptable salt thereof.

8. A method according to claim 5 employing 4-(benzoxazol-2-yl)-3-fluorophenylacetic acid or a pharmaceutically acceptable salt thereof.

9. The method according to claim 6 employing 2-[4-(benzoxazol-2-yl)-3-fluorophenyl]propionic acid or a pharmaceutically acceptable salt thereof.

10. A method according to claim 6 employing 2-[-(benzoxazol-2-yl) phenyl]propionic acid or a pharmaceutically acceptable salt thereof.

11. The method of claim 9 wherein the compound is the (d) isomer form or a pharmaceutically acceptable salt thereof.

12. A method according to claim 10 wherein the compound is in the (d) isomer form or a pharmaceutically acceptable salt thereof.

13. A pharmaceutical composition comprising a pharmaceutical carrier and an effective non-toxic amount of 0.1 to 50 mg per kilogram of body weight of a compound of the formula:

[Structure diagram]

or pharmaceutically acceptable salt thereof, wherein
R$_\alpha$ is hydrogen or methyl:
R$'_\alpha$ is hydrogen, or R$_\alpha$ and R$'_\alpha$ taken together can be methylene; or R$'_\alpha$ can be a methylene linkage attached to the unsubstituted ortho position of the benzenoid ring;
X, Y, R$_2$ and R$_3$ are the same or different and each is hydrogen, C$_{1-5}$alkyl, chloro, bromo, fluoro, and
R$_4$ is COOH, COOR, where R may be C$_{1-5}$alkyl, CONH$_2$,

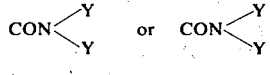

where Y may be C$_{1-3}$alkyl.

14. The composition according to claim 13 wherein the compound has the formula:

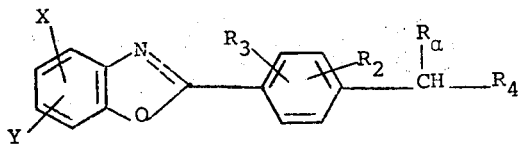

or pharmaceutically acceptable salt thereof, wherein
R$_\alpha$ is hydrogen or methyl;
X, Y, R$_2$ and R$_3$ are the same or different and each is hydrogen, C$_{1-5}$alkyl, chloro, bromo, fluoro, and
R$_4$ is COOH or COOR wherein R is C$_{1-5}$alkyl 15. A pharmaceutical composition comprising a pharmaceutical carrier and an effective non-toxic amount of a compound of the formula:

or pharmaceutically acceptable salt thereof, wherein
R$_\alpha$ is hydrogen or methyl;
R$_2$, R$_3$, X and Y are each hydrogen, chloro, bromo, or fluoro; and
R$_4$ is COOH; COOR, where R may be C$_{1-5}$alkyl, CONH$_2$; or where Y may be C$_{1-3}$alkyl.

16. The composition according to claim 15 wherein the compound has the formula:

or pharmaceutically acceptable salt thereof, wherein
R$_2$ and R$_3$ are each hydrogen or fluoro;
R$_\alpha$ is hydrogen or methyl;
R$_4$ is COOH or COOR wherein R is C$_{1-5}$ alkyl.

17. The composition according to claim 16 wherein the compound has the formula:

or pharmaceutically acceptable salt thereof, wherein R$_2$ and R$_3$ are each hydrogen or fluorine with at least one R being fluorine.

18. The composition according to claim 16 wherein the compound has the formula:

or pharmaceutically acceptable salt thereof wherein R$_2$ and R$_3$ are hydrogen or fluorine.

19. The composition according to claim 17 wherein the compound is 4-(benzoxazol-2-yl)-2-fluorophenylacetic acid or pharmaceutically acceptable salt thereof.

20. The composition according to claim 17 wherein the compound is 4-(benzoxazol-2-yl)-3-fluorophenylacetic acid or pharmaceutically acceptable salt thereof.

21. The composition according to claim 18 wherein the compound is 2-[4-(benzoxazol-2-yl)-3-fluorophenyl]-propionic acid or pharmaceutically acceptable salt thereof.

22. The composition according to claim 18 wherein the compound is 2-[4-(benzoxazol-2-yl)phenyl]propionic acid or pharmaceutically acceptable salt thereof.

23. The composition of claim 21 wherein the compound is in the (d) isomer form or pharmaceutically acceptable salt thereof.

24. The composition of claim 22 wherein the compound is in the (d) isomer form or pharmaceutically acceptable salt thereof.

* * * * *